United States Patent [19]

Eto et al.

[11] 4,450,109

[45] May 22, 1984

[54] THIAZINOBENZIMIDAZOLE DERIVATIVES

[75] Inventors: Hiromichi Eto, Abiko; Teruo Kohmoto, Chiba; Tadayuki Kouda, Narita; Youichiro Ogawa, Chiba; Susumu Sato, Chiba; Tadayuki Kuraishi, Chiba; Toshiaki Nakashima, Higashishisui, all of Japan

[73] Assignee: SS Pharmaceutical Co., Ltd., Tokyo, Japan

[21] Appl. No.: 417,596

[22] Filed: Sep. 13, 1982

Related U.S. Application Data

[62] Division of Ser. No. 240,219, Mar. 3, 1982, Pat. No. 4,369,309.

[30] Foreign Application Priority Data

Jun. 20, 1980 [JP] Japan ................... 55-83710

[51] Int. Cl.³ ........................... C07D 513/04
[52] U.S. Cl. .................... 260/243.3; 544/34
[58] Field of Search .............. 260/243.3; 544/34

[56] References Cited

U.S. PATENT DOCUMENTS 4,369,309   1/1983   Eto et al. ............................ 544/34

FOREIGN PATENT DOCUMENTS 57-9786   1/1982   Japan .................... 544/34
57-9787   1/1982   Japan .................... 544/34

Primary Examiner—John M. Ford
Attorney, Agent, or Firm—Oblon, Fisher, Spivak, McClelland & Maier

[57] ABSTRACT

The specification describes novel thiazinobenzimidazole derivatives represented by the general formula:

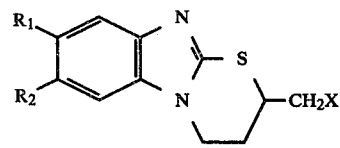

wherein $R_1$, $R_2$ and X represent a wide variety of substituent groups respectively. The above thiazinobenzimidazole derivatives may be prepared by reacting corresponding 2-hydroxymethyl thiazinobenzimidazole derivatives with corresponding reactive derivatives of carboxylic acid or halogenide or by reacting 2-p-toluenesulfonyloxymethyl-thiazinobenzimidazole derivatives with sodium azides, thiols, phenols or amines. The above thiazinobenzimidazole derivatives wherein X is OH may be prepared by reducing their corresponding 2-alkoxycarbonyl derivatives. Where X represents a p-toluenesulfonyloxy group, the thiazinobenzimidazole derivatives may be obtained by reacting corresponding 2-hydroxymethyl-thiazinobenzimidazole derivatives with p-toluenesulfonyl chloride. Where X stands for an N-substituted 2-(homo)piperazinomethyl group, 2-(homo)piperazinomethyl-thiazinobenzimidazole derivatives are reacted with reactive compounds to introduce the desired substituent groups. The thiazinobenzimidazole derivatives according to this invention are useful as medicament for circulatory systems.

1 Claim, No Drawings

THIAZINOBENZIMIDAZOLE DERIVATIVES

This is a division of application Ser. No. 240,219, filed Mar. 3, 1982, now U.S. Pat. No. 4,369,309.

BACKGROUND OF THE INVENTION

This invention relates to a novel thiazinobenzimidazole derivative, more particularly, to a thiazinobenzimidazole derivative represented by the general formula (I):

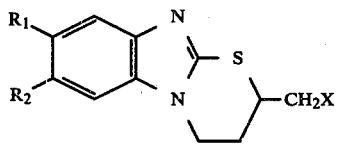

wherein $R_1$ and $R_2$ are each a hydrogen atom, alkyl group having 1 to 6 carbon atoms, alkoxy group having 1 to 6 carbon atoms or halogen atom, and X represents a hydroxy group, arylsulfonyloxy group, azide group, alkylcarbonyloxy group having 1 to 6 carbon atoms, arylcarbonyloxy group, thioether group, alkyloxy group having 1 to 6 carbon atoms, alkenyloxy group, aryloxy group, aralkyloxy group or

($R_3$ is a hydrogen atom, and $R_4$ is a hydrogen atom, alkyl group having 1 to 6 carbon atoms, alkyl group having 1 to 2 carbon atoms and substituted by a hydroxyl, alkyloxycarbonyl, cyclohexyl, furanyl or indolyl group, aryl, aralkyl or phenylamino group which may optionally contain one or more substituent groups; or $R_3$ and $R_4$ form together with the adjacent nitrogen atom a 5 to 8 membered ring which may optionally contain one or more additional nitrogen atoms or one or more oxygen atoms and which may also contain one or more substituent groups), and an acid addition salt thereof, as well as a process for the preparation of the same.

Many imidazole derivatives have heretofore been known. The present inventors have carried out various studies on certain thiazinoimidazole derivatives and found that the novel compounds represented by the above formula (I) pertain various effects to circulatory systems, more specifically, coronary vasodilating effect, peripheral vasodilating effect and mild hypotensive effect, resulting in the completion of the present invention.

SUMMARY OF THE INVENTION

Accordingly, this invention provides a novel thiazinobenzimidazole derivative (I) useful as a medicament for circulatory systems. Furthermore, the present invention also provides a novel process for the preparation of such a thiazinobenzimidazole derivative.

DETAILED DESCRIPTION OF PREFERRED EMBODIMENTS OF THE INVENTION

In the formula (I), X may be

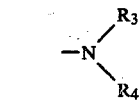

in which $R_3$ and $R_4$ may contain together with the adjacent nitrogen atom one or more additional nitrogen atoms or one or more oxygen atoms. Examples of groups forming 5 to 8-membered rings include pyrrolidino, piperidino, piperazino, homopiperazino, morpholino, hexamethyleneimino, and heptamethyleneimino groups, which may optionally be substituted by one or more other substituent groups. Such piperazino groups include those represented by the following formula:

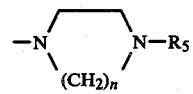

wherein $R_5$ denotes a hydrogen atom, alkyl group having 1 to 6 carbon atoms, hydroxyethyl group, cinnamoyl group which may optionally be substituted by a chlorine atom or a methyl, methoxy or methylenedioxy group, pyrrolidinocarbonylmethyl group, pyrrolidinopropyl group, trimethoxy phenylcarbonyloxypropyl group or trimethoxyphenylcarbonyl group, and n represents an integer of 2 or 3.

Needless to say, this invention encompasses all the isomers of the compounds represented by the above general formula (I).

A thiazinobenzimidazole derivative according to this invention can be prepared, for example, by either one of the following processes:

Process A

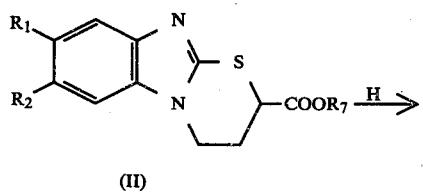

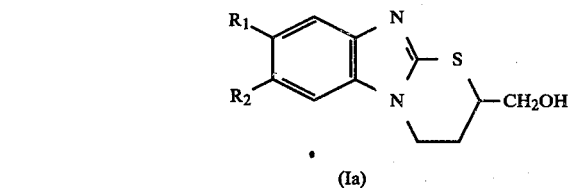

wherein $R_7$ represents an alkyl group, and $R_1$ and $R_2$ are as defined above.

A 2-hydroxymethyl-thiazinobenzimidazole derivative (Ia) is prepared by reducing a 2-alkoxycarbonyl-thiazinobenzimidazole derivative (II).

It is preferable to conduct the above reaction in a solvent such as ether, tetrahydrofuran or the like by using a reducing agent such as lithium aluminum hydride, sodium boron hydride, etc. The reaction is carried out while stirring the reaction mixture for several hours under ice-cooled conditions or at room temperature.

Process B

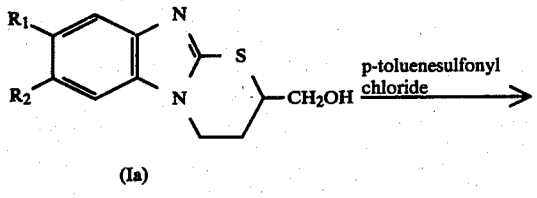

(Ia)

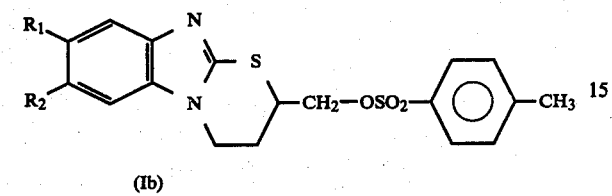

(Ib)

wherein $R_1$ and $R_2$ have the same meaning as defined above.

2-Hydroxymethyl-thiazinobenzimidazole derivative (Ia) is reacted with p-toluenesulfonyl chloride to produce 2-p-toluenesulfonyloxymethyl-thiazinobenzimidazole derivative (Ib).

This reaction is carried out in an inert solvent such as pyridine or the like under ice-cooling conditions or at room temperature for several hours while stirring the reaction mixture.

Process C

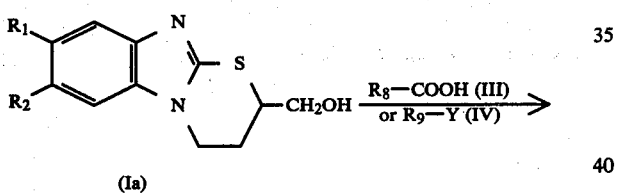

(Ia)

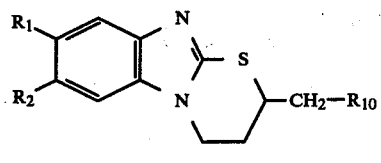

(Ic)

wherein $R_8$ represents an alkyl group having 1 to 6 carbon atoms or aryl group, $R_8$ denotes an alkyl group having 1 to 6 carbon atoms, alkenyl group or aralkyl group, $R_{10}$ is $R_8$—COO— or $R_9O$—, and Y indicates a halogen atom.

2-Hydroxymethyl-thiazinobenzimidazole derivative (Ia) is reacted with reactive derivative of the carboxylic acid (III) or halogenide (IV) to obtain a compound of the formula (Ic).

Among such reactive derivatives, there are for example acid halogenides, acid anhydrides, anhydrides of acid mixtures, activated esters, etc.

The reaction between the compound (Ia) and that having the formula (IV) is preferably carried out in an inert solvent, in the presence of a base, at a temperature from room temperature to 60° C., for several hours. As the solvent, may be used tetrahydrofuran, dimethyl-formamide, ether, benzene, chloroform, dichloromethane, etc. whereas the base may be sodium hydride, sodium hydroxide, potassium hydroxide, sodium carbonate, potassium carbonate, etc.

It is preferable to carry out the reaction between the compounds (Ia) and (III) in the presence of a base such as pyridine or the like, under ice-cooling conditions or at room temperature, for several hours.

Process D

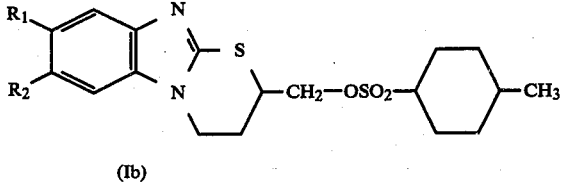

(Ib)

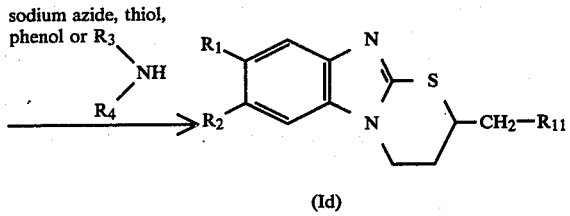

(Id)

wherein $R_{11}$ is an azide, thioether, phenoxy group or

($R_3$ and $R_4$ are as defined above), and $R_1$ and $R_2$ are also as defined above.

2-p-Toluenesulfonyloxymethyl-thiazinobenzimidazole derivative (Ib) is reacted with sodium azide, a thiol, phenol or amine to produce the compound having the formula (Id).

The above reaction is carried out by refluxing the reactant for several to about 15 hours in an inert solvent or without any solvent, or by heating the same in a sealed tube. As the solvent, chloroform, methylene chloride, dioxane, benzene, tetrahydrofuran, dimethylformamide, dimethylsulfoxide, or the like may be used. A base such as sodium hydride may also be added to increase the yield.

Process E

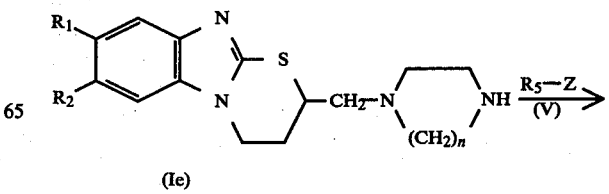

(Ie)

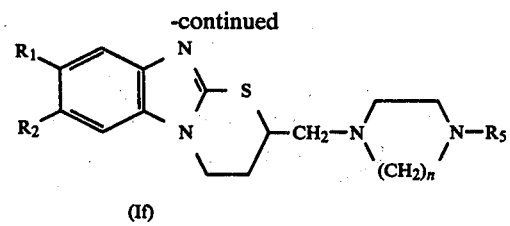

(If)

wherein Z is a reactive group, n represents an integer of 2 or 3, and $R_1$, $R_2$ and $R_5$ are as defined above.

2-(Homo)piperazinomethyl-thiazinobenzimidazole derivative (Ie) is reacted with a compound (V) to form a compound (If).

The reactive group represented by Z may preferably be a halogen atom where $R_5$ is an alkyl group having 1 to 6 carbon atoms, hydroxyethyl group, pyrrolidinocarbonylmethyl group, pyrrolidinopropyl group, or trimethoxyphenylcarbonyloxypropyl group or a halogen atom, residue or acid anhydride of mixed acid anhydride where $R_5$ denotes a cinnamoyl or trimethoxyphenylcarbonyl group.

The reaction is carried out by stirring the reaction mixture in an inert solvent, in the presence of a base, at room temperature, for several hours. As the solvent, chloroform, methylenechloride, acetone, benzene, etc. may be used, while the base may be triethylamine, pyridine, potassium carbonate, sodium carbonate, sodium bicarbonate, sodium hydroxide, potassium hydroxide, or the like.

The thus-obtained thiazinobenzimidazole derivatives according to this invention may be converted to their inorganic salts such as hydrochlorides, hydrobromides, perchlorates or the like, or their organic salts such as fumarates, succinates, tartarates, maleates, oxalates or the like.

Effects of the thus-obtained compounds of this invention on the circulatory systems were tested, giving the following results:

Vasodilating and hypotensive actions (1) Intraarterial (i.a.) administration:

Male mongrel dogs (15–26 kg) were anesthetized with sodium pentobarbiturate (30 mg/kg i.v.), and respirated artificially. Femoral blood flow (FBF) was measured by an electromagnetic flowmeter via a flow probe around the right femoral artery. Blood pressure was measured by a pressure transducer through a polyethylene cannula inserted into the left femoral artery, and heart rate was measured by a cardiotachograph from the R—R intervals of electrocardiograph. These parameters were recorded on a polygraph. Compounds of this invention were dissolved in ethanol-dilute hydrochloric acid solution-saline, and a reference compound (paraverine hydrochloride: Pap) was dissolved in saline. 0.03–0.033 ml/kg of each sample was injected i.a. in about 3 seconds. The values for $FBF_{50}$, the dose which increases FBF by 50% of the basal level, of these compounds were calculated from the measured values, and compared with that of Pap. Relative potencies of compounds of this invention are shown in Table 1. The compounds of this invention exhibited activity as potent as or more potent than that of Pap.

TABLE 1

| | Compound tested [in the formula (I)] | | | $FBF_{50}$ relative potency |
|---|---|---|---|---|
| | $R_1$ | $R_2$ | X | |
| Compounds according to this invention | H | H | $-NHC_3H_7-n$ | 0.59 |
| | " | " | -N (pyrrolidine) | 1.10 |
| | " | " | -N (piperidine) | 3.49 |
| | " | " | -N (4-methylpiperidine)-CH₃ | 3.40 |
| | " | Cl | " | 2.40 |
| | " | CH₃ | " | 4.48 |
| | " | OCH₃ | " | 2.30 |
| | CH₃ | CH₃ | " | 3.0 |
| | H | H | -N(piperazine)N-C(=O)-CH=CH-(3,4,5-trimethoxyphenyl) | 0.16 |
| Reference compound | | | Papaverine hydrochloride | 1.0 |

(2) Intravenous (i.v.) administration:

In open chest dogs, the left coronary descending artery and vertebral artery were exposed, and these blood flow (CBF and VBF) were measured in a similar manner to (1). 1 mg/kg i.v. of compounds of this invention increased CBF and VBF, and caused mild hypotension. Relative potencies of these compounds to those of Pap are shown in Table 2.

Among the compounds according to this invention, that represented by $R_1=R_2=$ hydrogen and

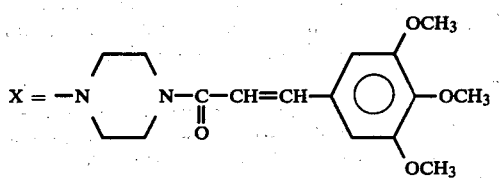

and that represented by $R_1=R_2=$ hydrogen and

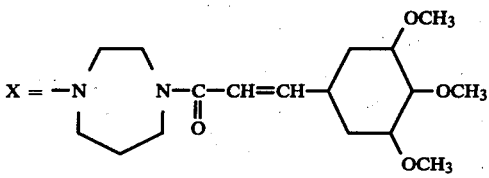

showed a selective coronary vasodilating action. The action of these two compounds was equipotent to that of Pap, but the duration was long-lasting contrary to that of Pap. Therefore, these compounds are useful as a coronary vasodilator and hypotensive drug.

Pap increased heart rate at 1 mg/kg i.v., while the compounds of this invention did not increase but slightly decreased heart rate.

TABLE 2

| | | Compound tested [in the formula (I)] | | VBF relative potency | CBF relative potency |
|---|---|---|---|---|---|
| | $R_1$ | $R_2$ | X | | |
| Compounds according to this invention | H | H | 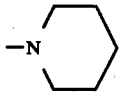 | 0.3 | 0.3 |
| | " | " | 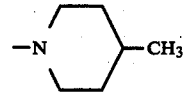 | 1.0 | — |
| | " | CH$_3$ | 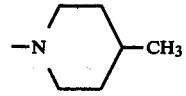 | 3.0 | >0.3 |
| | " | " | 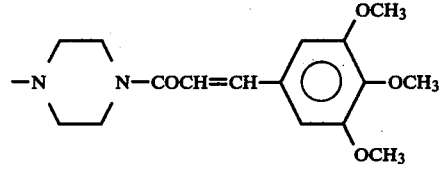 | >0.1 | 1.0* |
| | " | " | 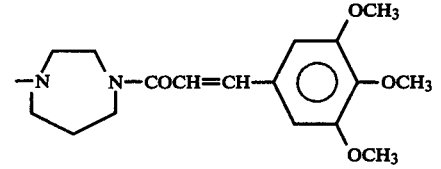 | >0.1 | 1.0* |
| | " | " | 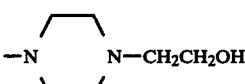 | 0.5 | — |
| Reference compound | | | Papaverine hydrochloride | 1.0 | 1.0 |

*long lasting

Now, the present invention is described further in reference to the following examples.

EXAMPLE 1

3,4-Dihydro-2-hydroxymethyl-2H-(1,3)-thiazino[3,2-a]benzimidazole

To a solution of 2.48 g (10 m mole) of 3,4-dihydro-2-methoxycarbonyl-2H-(1,3)-thiazino-[3,2-a]benzimidazole in dry tetrahydrofuran (50 ml) was added dropwise 0.5 g of lithium aluminum hydride devided in small pieces, with stirring under ice cooling condition. After thirty minutes, the resultant complex was decomposed by the addition of hydrated tetrahydro furan and subjected to filtration. Subsequent to drying the filtrate over anhydrous magnesium sulfate, tetrahydrofuran was evaporated under reduced pressure. The residue was chromatographed on silica gel and eluted with chloroform to obtain 1.2 g (yield: 54.5%) of the intended product, m.p. 112°–113° C.; IR $\nu_{max}^{KBr}$ cm$^{-1}$: 3500–3000, 1430; Anal. Calcd. for $C_{11}H_{12}N_2OS$: C, 59.98; H, 5.49; N, 12.72; S, 14.55; Found: C, 59.71; H, 5.61, N, 12.99; S, 14.15.

EXAMPLE 2

3,4-Dihydro-2-p-toluenesulfonyloxymethyl-2H-(1,3)-thiazino[3,2-a]benzimidazole

To a solution of 1.1 g (5 m mole) of 3,4-dihydro-2-hydroxymethyl-3H-(1,3)-thiazino[3,2-a]benzimidazole in dry pyridine (10 ml) was slowly added one gram of p-toluenesulfonyl chloride with stirring under ice cooling condition. The solution was stirred at the same temperature for a while, then allowed to rise to room temperature and stirred for further one hour. The reaction mixture was poured into ice water and precipitated crystals were filtered off. The crystals were washed with water, and n-hexane, and dried, to obtain 1.18 g (yield: 62%) of the intended product, m.p. 145°–147° C.; IR $\nu_{max}^{KBr}$ cm$^{-1}$: 3100–2960, 1400, 1170; Anal. Calcd. for $C_{18}H_{18}N_2O_3$: C, 57.73; H, 4.84; N, 7.48; S, 17.12; Found: C, 57.61; H, 4.93; N, 7.69; S, 16.84.

EXAMPLE 3

3,4-Dihydro-2-isoprenyloxymethyl-2H-(1,3)-thiazino[3,2-a]benzimidazole

To a solution of one gram of 3,4-dihydro-2-hydroxymethyl-2H-(1,3)-thiazino[3,2-a]benzimidazole in dry tetrahydrofuran (20 ml) was treated with 0.5 g of 50% sodium hydride containing mineral oil at 0° C. under stirring. The mixture was stirred for 1 hr, then one gram of isoprenylbromide was added, and the stirring was continued for three hours at room temperature. The reaction mixture was condensed under reduced pressure. The residue was added with water and then extracted with chloroform, and dried over anhydrous magnesium sulfate. Chloroform was evaporated under reduced pressure. The residue was chromatographed on silica gel and eluted with chloroform to obtain 0.42 g (yield: 30%) of the intended product, m.p. 56°–60° C.; IR $\nu_{max}^{KBr}$ cm$^{-1}$: 3100–2850, 1600, 1420; Anal. Calcd. for $C_{16}H_{20}N_2OS$: C, 66.63; H, 6.99; N, 9.71; S, 11.12; Found: C, 66.64; H, 6.92; N, 9.94; S, 10.89.

EXAMPLE 4

3,4-Dihydro-2-aminomethyl-2H-(1,3)-thiazino[3,2-a]benzimidazole

To 2.24 g of 3,4-dihydro-2-p-toluenesulfonyloxymethyl-2H-(1,3)-thiazino[3,2-a]benzimidazole, were added 5 g of 25% ammonia water and 40 ml of dioxane. The mixture were heated in a sealed tube, at 120° C., for 75 hours. The reaction mixture was then condensed under reduced pressure. The residue was added with water and then extracted with chloroform, and dried over anhydrous magnesium sulfate. Chloroform was evaporated under reduced pressure. The residue was chromatographed on silica gel and eluted with chloroform to obtain 0.46 g (yield: 35.1%) of the intended product, m.p. 217°–222° C.; IR $\nu_{max}^{KBr}$ cm$^{-1}$ 3300–2600, 1440; Anal. Calcd. for $C_{11}H_{13}N_3S$: C, 60.25; H, 5.97; N, 19.16; S, 14.62; Found: C, 60.28; H, 5.99; N, 19.60; S, 14.13.

EXAMPLE 5

3,4-Dihydro-2-n-butylaminomethyl-2H-(1,3)-thiazino[3,2-a]benzimidazole

To a solution of 2.24 g of 3,4-dihydro-2-p-toluenesulfonyloxymethyl-2H-(1,3)-thiazino[3,2-a]benzimidazole in chloroform (30 ml) was added 4 ml of n-butylamine. A catalytic amount of sodium hydride was thereafter added under ice-cooling, stirring conditions. After stirring for 15 minutes at room temperature, the mixture was refluxed for 24 hours. The reaction mixture was cooled and then condensed under reduced pressure. The residue was added with water and extracted with chloroform. The extract was washed with water, dried over anhydrous magnesium sulfate. Chloroform was evaporated under reduced pressure. The residue was chromatographed on silica gel and eluted with chloroform to obtain 0.71 g (yield: 43.3%) of the intended product, m.p. 122°–124° C.; IR $\nu_{max}^{KBr}$ cm$^{-1}$: 3320, 3100–2700, 1430; Anal. Calcd. for $C_{15}H_{21}N_3S$: C, 65.42; N, 7.68; N, 15.26; S, 11.64; Found: C, 65.63; H, 7.61; N, 15.46; S, 11.30.

EXAMPLE 6

3,4-Dihydro-2-benzylaminomethyl-2H-(1,3)-thiazino[3,2-a]benzimidazole

To a solution of 1.12 g of 3,4-dihydro-2-p-toluenesulfonyloxymethyl-2H-(1,3)-thiazino[3,2-a]benzimidazole in chloroform (20 ml) was added with 0.41 g of benzylamine and a catalytic amount of sodium hydride, and refluxed for 11 hours. The reaction mixture was cooled and then condensed under reduced pressure. The residue was added with water, extracted with chloroform. The extract was washed with water, and dried over anhydrous magnesium sulfate. Chloroform was evaporated under reduced pressure. The residue was chromatographed on silica gel and eluted with chloroform to obtain 0.29 g (Yield: 31%) of the intended product, m.p. 155°–156° C.; IR $\nu_{max}^{KBr}$ cm$^{-1}$: 3260, 3100–2800, 1600, 1420; Anal. Calcd. for $C_{18}H_{19}N_3S$: C, 69.87; H, 6.19; N, 13.58; S, 10.36; Found: C, 70.00; H, 6.21; N, 13.69; S, 10.10.

EXAMPLE 7

3,4-Dihydro-2-(p-methoxyphenyl)aminomethyl-2H-(1,3)-thiazino[3,2-a]benzimidazole 3,4-Dihydro-2-p-toluenesulfonyloxymethyl-2H-(1,3)-thiazino[3,2-a]benzimidazole in the amount of 1.12 g (3 m mole) was dissolved in 30 ml of chloroform. Then, 0.44 g of p-anisidine (3.6 m mole) and a catalytic amount of sodium hydride were added under ice-cooled stirring conditions. The temperature of the mixture was allowed to rise to room temperature, and then refluxed for 12 hours. The reaction mixture was cooled and washed with water. After drying the chloroform layer over anhydrous magnesium sulfate, chloroform was evaporated under reduced pressure. The residue was chromatographed on silica gel and eluted with chloroform to obtain 0.28 g (yield: 31%) of the intended product, m.p. 155°–157° C.; IR $\nu_{max}^{KBr}$ cm$^{-1}$: 3360, 3100–2800, 1430; Anal. Calcd. for $C_{18}H_{19}N_3OS$: C, 66.44; H, 5.88;

N 12.91; S, 9.85; Found: C, 66.91; H, 5.90; N, 12.88; S, 9.70.

EXAMPLE 8

3,4-Dihydro-2-diethylaminomethyl-2H-(1,3)-thiazino[3,2-a]benzimidazole

Into 20 ml of tetrahydrofuran was dissolved 1.12 g (3 m mole) of 3,4-dihydro-2-p-toluenesulfonyloxymethyl-2H-(1,3)-thiazino[3,2-a]benzimidazole, followed by the addition of 5 ml of diethylamine. Then, a catalytic amount of sodium hydride was added under ice-cooled stirring conditions. The temperature of the mixture was allowed to rise to room temperature and then refluxed for eight hours. The reaction mixture was cooled and then condensed under reduced pressure. The reaction product was added with water and then extracted with chloroform. The chloroform layer was then dried over anhydrous magnesium sulfate. Chloroform was evaporated under reduced pressure. The residue was chromatographed on silica gel and eluted with chloroform to obtain 0.33 g (yield: 40%) of the intended product, m.p. 93°-94° C.; IR $\nu_{max}^{KBr}$ cm$^{-1}$: 3100–2800, 1420; Anal. Calcd. for $C_{15}H_{21}N_3S$: C, 65.42; H, 7.68; N, 15.26; S, 11.64; Found: C, 65.33; H, 7.77; N, 15.49; S, 11.41.

EXAMPLE 9

3,4-Dihydro-2-dipropylaminomethyl-2H-(1,3)-thiazino[3,2-a]benzimidazole

To 1.12 g of 3,4-dihydro-2-p-toluenesulfonyloxymethyl-2H-(1,3)-thiazino[3,2-a]benzimidazole were added 4 ml of di-n-propylamine and 20 ml of dioxane. The mixture was reacted in a sealed tube, at 120° C. and for 67 hours. After cooling down the temperature of the reaction mixture, it was condensed under reduced pressure. Water was added to the condensed reaction mixture, followed by an extraction with chloroform and dried over anhydrous magnesium sulfate. Chloroform was evaporated under reduced pressure and the residue was chromatographed on silica gel and eluted with chloroform to obtain 0.13 g (yield: 14.3%) of the intended product, m.p. 82°-84° C.; IR $\nu_{max}^{KBr}$ cm$^{-1}$: 3100–2700, 1420; Anal. Calcd. for $C_{17}H_{25}N_3S$: C, 67.29; N, 8.30; N, 13.85; S, 10.56; Found: C, 67.52; H, 8.41; N, 13.98; S, 10.09.

EXAMPLE 10

3,4-Dihydro-2-piperazinomethyl-2H-(1,3)-thiazino[3,2-a]benzimidazole

To 30 ml of chloroform were dissolved 3 g of 3,4-dihydro-2-p-toluenesulfonyloxymethyl-2H-(1,3)-thiazino[3,2-a]benzimidazole and 10 g of piperazine. The resultant solution was refluxed for 18 hours. The reaction mixture was cooled, added with water and then extracted with chloroform, followed by washing the chloroform layer and dried over anhydrous magnesium sulfate. Chloroform was evaporated under reduced pressure and the residue was chromatographed on silica gel and eluted with chloroform to obtain 1.2 g (Yield: 51%) of the intended product, m.p. 151°-153° C.; IR $\nu_{max}^{KBr}$ cm$^{-1}$: 3600–3000, 3100–2800, 1420; Anal. Calcd. for $C_{15}H_{20}N_4S$: C, 62.47; L H, 6.99; N, 19.43; S, 11.11; Found: C, 62.41; H, 7.01; N, 19.70; S, 10.88.

EXAMPLE 11

3,4-Dihydro-2-homopiperazinomethyl-2H-(1,3)-thiazino[3,2-a]benzimidazole

To 50 ml of chloroform was dissolved 3.74 g of 3,4-dihydro-2-p-toluenesulfonyloxy-2H-(1,3)-thiazino[3,2-a]benzimidazole, followed by the addition of 3 g of homopiperazine and a catalytic amount of sodium hydride. The mixture was refluxed for 15 hours. The reaction mixture was cooled, added with water and extracted with chloroform. The thus-obtained chloroform layer was washed with water and then dried over anhydrous magnesium sulfate. Chloroform was evaporated under reduced pressure and the residue was chromatographed on silica gel and eluted with chloroform to obtain 1.23 g (Yield: 40%) of the intended product, m.p. 132°-135° C.; IR $\nu_{max}^{KBr}$ cm$^{-1}$: 3400–3200, 3050–2700, 1420; Anal. Calcd. for $C_{16}H_{22}N_4S$: C, 63.54; H, 7.33; N, 18.53; S, 10.60; Found: C, 63.61; H, 7.38; N, 18.69; S, 10.32.

EXAMPLE 12

1[(3,4-Dihydro-2H-(1,3)-thiazino[3,2-a]benzimidazole-2-yl)methyl]-4-(2-hydroxyethyl)piperazine To 1.12 g of 3,4-dihydro-2-p-toluenesulfonyloxymethyl-2H-(1,3)-thiazine[3,2-a]benzimidazole, were added 2 g of piperazine ethanol and 10 ml of chloroform. The mixture was refluxed for 10 hours. The reaction mixture was cooled, added with water and then extracted with chloroform. The resultant chloroform layer was washed with water and dried over anhydrous magnesium. Chloroform was evaporated under reduced pressure and the residue was chromatographed on silica gel and eluted with chloroform to obtain 0.42 g (Yield: 43%) of the intended product, m.p. 68°-70° C.; IR $\nu_{max}^{KBr}$ cm$^{-1}$: 3000–2750, 1425; Anal. Calcd. for $C_{17}H_{24}N_4OS$: C, 61.42; H, 7.28; N, 16.85; S, 9.64; Found: C, 61.22; H, 7.39; N, 16.99; S, 9.33.

EXAMPLE 13

3,4-Dihydro-2-(4'-methylpiperizino)Methyl-2H-(1,3)-thiazino[3,2-a]benzimidazole Ten milliliters of 4-pipecoline was added to 1.12 g of 3,4-dihydro-2-p-toluenesulfonyloxy-2H-(1,3)-thiazino[3,2-a]benzimidazole and heated at 60°-70° C. for 10 hours. The reaction product was cooled and then condensed under reduced pressure, followed by the addition of water and an extraction with chloroform. The resultant chloroform layer was dried over anhydrous magnesium sulfate. Chloroform was evaporated under reduced pressure and the residue was chromatographed on silica gel and eluted with chloroform to obtain 0.51 g (Yield: 56%) of the intended product, m.p. 133°-134° C.; IR $\nu_{max}^{KBr}$ cm$^{-1}$: 2950–2800, 1420; Anal. Calcd. for $C_{17}H_{23}N_3S$: C, 67.73, H, 7.69; N, 13.94; S, 10.64; Found: C, 67.71; H, 7.80; N, 13.77; S, 10.63.

EXAMPLE 14

1-[(3,4-Dihydro-2H-(1,3)-thiazino[3,2-a]benzimidazole-2-yl)methyl]-4-[(1-pyrrolidinocarbonyl)methyl]piperazine To 20 ml of chloroform was dissolved 1.0 g of 3,4-dihydro-2-piperazinomethyl-2H-(1,3)-thiazino[3,2-a]benzimidazole, followed by the addition of 0.4 g of 1-chloroacetylpyrrolidine under ice-cooling conditions. Thereafter, 0.5 ml of triethylamine was added dropwise.

The mixture was stirred at room temperature for 8 hours. After the completion of the reaction, the reaction mixture was added with water and then extracted with chloroform. The resultant chloroform layer was dried over anhydrous magnesium sulfate. Chloroform was evaporated under reduced pressure and the residue was chromatographed on silica gel and eluted with chloroform to obtain 0.57 g (Yield: 41%) of the intended product, m.p. 159°–162° C.; IR $\nu_{max}^{KBr}$ cm$^{-1}$: 3000–2800, 1640, 1420; Anal. Calcd. for $C_{21}H_{29}N_5OS$: C, 63.13; H, 7.32; N, 17.53; S, 8.02; Found C, 63.11; H, 7.35; N, 17.71; S, 7.91.

EXAMPLE 15

1-[(3,4-Dihydro-2H(1,3)-thiazino[3,2-a]benzimidazole-2-yl)methyl]-4-(3,4,5-trimethoxycinnamoyl)piperazine To 20 ml of chloroform was dissolved 1.0 g (3.5 m mole) of 3,4-dihydro-2-piperazinomethyl-2H-(1,3)-thiazine[3,2-a]benzimidazole, followed by the dropwise addition of 1 g of 3,4,5-trimethoxycinnamoyl chloride in 10 ml of chloroform under ice-cooled stirring conditions. After ten minutes, 0.5 ml of triethylamine was added. The mixture was stirred for 3 hours at room temperature. After the completion of the reaction, the reaction mixture was added with water and extracted with chloroform. The chloroform layer was washed with water and then dried over anhydrous magnesium sulfate. Chloroform was evaporated under reduced pressure and the residue was chromatographed on silica gel and eluted with chloroform to obtain 1.2 g (Yield: 69.4%) of the intended product, m.p. 211°–212° C.; IR $\nu_{max}^{KBr}$ cm$^{-1}$: 3000–2800, 1640, 1575, 1420; Anal. Calcd. for $C_{27}H_{32}N_4O_4S$: C, 63.76; H, 6.34; L N, 11.02; S, 6.30; Found: C, 63.51; H, 6.49; N, 10.94; S, 5.91.

EXAMPLE 16

1-[(3,4-Dihydro-2H(1,3)-thiazino[3,2-a]benzimidazole 2yl)methyl]-4-(3,4,5-trimethoxycinnamoyl)homopiperazine To 20 ml of chloroform was dissolved 0.6 g of 3,4-dihydro-2-homopiperazinomethyl-2H-(1,3)-thiazino[3,2-a]benzimidazole, followed by the addition of 0.6 g of 3,4,5-trimethoxycinnamoyl chloride under ice-cooled stirring conditions. After ten minutes, 0.3 ml of triethylamine was added further. The mixture was stirred at room temperature for 3 hours. The reaction mixture was washed with water and dried over anhydrous magnesium sulfate. Chloroform was evaporated under reduced pressure and the residue was chromatographed on silica gel and eluted with chloroform to obtain 0.32 g (Yield: 31%) of the intended product, m.p. 107°–110° C.; IR $\nu_{max}^{KBr}$ cm$^{-1}$: 3100–2700, 1635, 1570, 1420; Anal. Calcd. for $C_{28}H_{34}N_4O_4S$: C, 63.35; H, 6.56; N, 10.72; S, 6.13; Found: C, 63.31; H, 6.50; N, 10.91; S, 5.99.

EXAMPLE 17

3,4-Dihydro-2-azidemethyl-2H-(1,3)-thiazino[3,2-a]benzimidazole

Fifteen milliliters of dimethylsulfoxide was added to 1.12 g (3 m mole) of 3,4-dihydro-2-p-toluenesulfonyloxymethyl-2H-(1,3)-thiazino[3,2-a]benzimidazole and 0.39 g (6 m mole) of sodium azide. The mixture was heated at 110° C. for 3 hours. After cooling, dimethylsulfoxide was evaporated under reduced pressure. The residue was added with water and extracted with chloroform. The chloroform layer was dried over anhydrous magnesium sulfate. Thereafter, chloroform was evaporated under reduced pressure, to obtain 0.45 g (Yield: 61%) of the intended product, m.p. 95°–97° C.; IR $\nu_{max}^{KBr}$ cm$^{-1}$: 3100, 2900, 2100, 1440; Anal. Calcd. for $C_{11}H_{11}N_5S$: C, 53.86; H, 4.52; N, 28.55; S, 13.07; Found: C, 53.80; H, 4.61; N, 28.70; S, 12.89.

EXAMPLE 18

3,4-Dihydro-2-benzylthiomethyl-2H-(1,3)-thiazino[3,2-a]benzimidazole

To 1.12 g (m mole) of 3,4-dihydro-2-p-toluenesulfonyloxy-2H-(1,3)-thiazino[3,2-a]benzimidazole and 0.38 g (3 m mole) of benzylmercaptane, were added 10 mg of 50% sodium hydride and 20 ml of dimethylformamide. The mixture was heated at 70° C. for 10 hours. After cooling, dimethylformamide was evaporated under reduced pressure and the residue was washed twice with n-hexane. The residue was then added with water, extracted with chloroform and dried over anhydrous magnesium sulfate. Chloroform was evaporated under reduced pressure, to obtain 0.21 g (Yield: 21%) of the intended product, m.p. 97°–99° C.; IR $\nu_{max}^{KBr}$ cm$^{-1}$: 3100–2850, 1440; Anal. Calcd. for $C_{18}H_{18}N_2S_2$: C, 66.22; H, 5.56; N, 8.58; S, 19.64; Found: C, 66.33; H, 5.57; N, 8.77; S, 19.33.

EXAMPLES 19–74

Similarly, the following compounds were prepared.

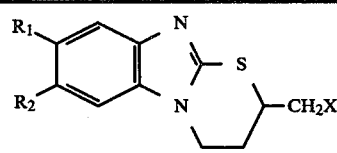

| Example | Compound R₁ | R₂ | X | Melting point (°C.) | IR $\nu_{max}^{KBr}$ cm$^{-1}$ |
|---|---|---|---|---|---|
| 19 | H | CH₃ | —OH | oil | 3500–2800, 3100–2850, 1435 |
| 20 | " | Cl | " | oil | 3500–2600, 3000–2800, 1430 |
| 21 | " | OCH₃ | " | oil | 3500–2800, 3000–2850, 1440 |
| 22 | CH₃ | CH₃ | " | 160–162 | 3500–2800, 1440 |
| 23 | H | CH₃ | 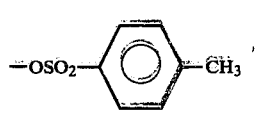 | 104–106 | 3100–2900, 1440 |

-continued
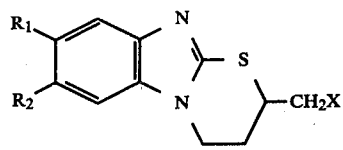
| Example | R₁ | R₂ | X | Melting point (°C.) | IR $\nu_{max}^{KBr}$ cm$^{-1}$ |
|---|---|---|---|---|---|
| 24 | " | Cl | " | 138–139 | 3100–2850, 1435 |
| 25 | " | OCH₃ | " | 85–87 | 3100–2850, 1435 |
| 26 | CH₃ | CH₃ | " | 139–141 | 3100–2850, 1435 |
| 27 | H | H | —SCH₂CO₂C₂H₅ | oil | 3100–2850, 1730, 1430 |
| 28 | H | H | (S-C(=N-CH=CH-)N-ph thiazole) | oil | 3100–2900, 1600, 1430 |
| 29 | " | " | —NHCH₃ | 146–148 | 3330, 3100–2700, 1430 |
| 30 | " | " | —NHC₂H₅ | 124–126 | 3320, 3100–2700, 1425 |
| 31 | " | " | —NH n-C₃H₇ | 107–108 | 3100–2800, 1420 |
| 32 | " | " | —NH i-C₃H₉ | 168–170 | 3300, 3100–2700, 1425 |
| 33 | " | " | —NH i-C₄H₉ | 124–126 | 3290, 3100–2700, 1415 |
| 34 | " | " | —NHCH₂CH₂OH | 166–168 | 3300, 3270, 3000–2700, 1425 |
| 35 | " | " | —NHCH₂-cyclohexyl | 163–164 | 3300, 3100–2700, 1420 |
| 36 | " | " | —NHCH(CH₃)CO₂CH₃ | oil | 3300, 3100–2800, 1730, 1420 |
| 37 | " | " | —NHCH₂-(2-furyl) | 120–121 | 3260, 3100–2700, 1420 |
| 38 | " | " | —NHCH₂CH₂-(3-indolyl) | 178–179 | 3300–2700, 1420 |
| 39 | " | " | —NH-phenyl | 188–189 | 3360, 3100–2850, 1600, 1430 |
| 40 | " | " | —NH-(2-CH₃-phenyl) | 140–143 | 3300, 3100–2900, 1600, 1440 |
| 41 | " | " | —NH-(4-CH₃-phenyl) | 191–193 | 3325, 3100–2800, 1420 |
| 42 | " | " | —NH-(4-Cl-phenyl) | 195–196 | 3380, 3100–2900, 1430 |
| 43 | " | " | —N(CH₃)₂ | 142–144 | 3100–2600, 1435 |
| 44 | " | " | —N(i-C₃H₇)₂ | 139–142 | 3100–2700, 1425 |

-continued
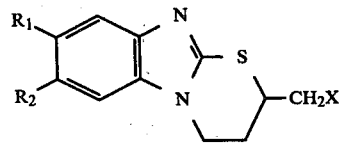
| Example | R₁ | R₂ | Compound X | Melting point (°C.) | IR $\nu_{max}^{KBr}$ cm$^{-1}$ |
|---|---|---|---|---|---|
| 45 | " | " | —N(pyrrolidine) | 143–144 | 2950, 2800, 1420 |
| 46 | " | " | —N(piperidine) | 153–155 | 2950–2850, 1420 |
| 47 | " | " | —N(hexamethyleneimine) | 161–162 | 3100–2850, 1420 |
| 48 | " | " | —N(heptamethyleneimine) | 156–158 | 3100–2850, 1420 |
| 49 | " | " | —N(2-methylpiperidine), CH₃ | 126–128 | 3100–2750, 1420 |
| 50 | " | " | —N(3-methylpiperidine), CH₃ | 132–133 | 3100–2700, 1420 |
| 51 | " | " | —N(3-hydroxypiperidine), OH | 169–171 | 3600–3200, 3100–2850, 1420 |
| 52 | " | " | —N(4-carbethoxypiperidine)—CO₂C₂H₅ | 119–121 | 3000–2750, 1730, 1420 |
| 53 | " | " | —N(4-benzylpiperidine)—CH₂ph | 162–163 | 3000–2800, 1420 |
| 54 | " | " | —N(morpholine)O | 138–139 | 2950–2800, 1420 |
| 55 | " | " | —N(4-methylpiperazine)N—CH₃ | 131–133 | 3100–2750, 1420 |

-continued

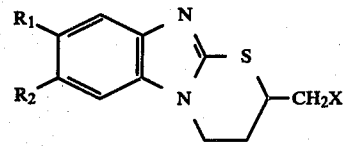

| Example | Compound R₁ | R₂ | X | Melting point (°C.) | IR $\nu_{max}^{KBr}$ cm$^{-1}$ |
|---|---|---|---|---|---|
| 56 | " | " | —N(piperazine)N—CH₂CH₂CH₂—N(pyrrolidine) | 141–143 | 3100–2850, 1420 |
| 57 | " | " | —N(piperazine)N—CH₂CH₂CH₂OC(=O)-3,4,5-trimethoxyphenyl | 117–119 | 2950, 2800, 1710, 1420 |
| 58 | " | " | —N(piperazine)N—C(=O)-3,4,5-trimethoxyphenyl | 230–232 | 3100–2750, 1630, 1420 |
| 59 | " | " | —N(piperazine)N—C(=O)—CH=CH—phenyl | 167–171 | 3100–2700, 1640, 1590, 1420 |
| 60 | " | " | —N(piperazine)N—C(=O)—CH=CH—(4-CH₃-phenyl) | 190–192 | 3050–2700, 1640, 1595, 1420 |
| 61 | " | " | —N(piperazine)N—C(=O)—CH=CH—(4-OCH₃-phenyl) | 187–189 | 3100–2700, 1640, 1590, 1420 |
| 62 | " | " | —N(piperazine)N—C(=O)—CH=CH—(3,4-dimethoxyphenyl) | 199–201 | 3100–2800, 1635, 1590, 1420 |
| 63 | " | " | —N(piperazine)N—C(=O)—CH=CH—(3,4-methylenedioxyphenyl) | 205–208 | 3100–2750, 1635, 1590, 1420 |
| 64 | " | CH₃ | —N(4-methylpiperidine) | 167–169 | 2950–2850, 1425 |
| 65 | " | Cl | —N(4-methylpiperidine) | 146–148 | 2950–2700, 1420 |

-continued

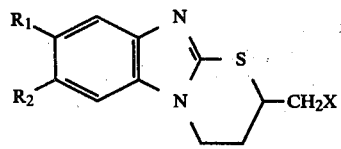

| Example | R₁ | R₂ | X | Melting point (°C.) | IR $\nu_{max}^{KBr}$ cm⁻¹ |
|---|---|---|---|---|---|
| 66 | " | OCH₃ | -N⟨piperidine⟩-CH₃ | 126-128 | 2950-2700, 1430 |
| 67 | CH₃ | CH₃ | -N⟨piperidine⟩-CH₃ | 218-219 | 2950-2700, 1430 |
| 68 | H | H | -NHNH-C₆H₅ | 170-171 | 3360, 3330, 1420 |
| 69 | " | " | -OCH₃ | 82-83 | 3100-2800, 1430 |
| 70 | " | " | -OCH₂-C₆H₅ | 96-98 | 3100-2800, 1430 |
| 71 | " | " | -O-C₆H₅ | 141-143 | 3100-2800, 1600, 1425 |
| 72 | " | " | -OC(=O)-CH₃ | 145-146 | 3100-2850, 1740, 1420 |
| 73 | " | " | -OC(=O)-C₆H₂(OCH₃)₃ | oil | 3100-2850, 1720, 1420 |
| 74 | " | " | -N⟨piperazine⟩N-C(=O)CH=CH-C₆H₄-Cl | 227-229 | 3050-2750, 1640, 1595, 1420 |

What is claimed is:

1. A thiazinobenzimidazole derivative represented by formula (I):

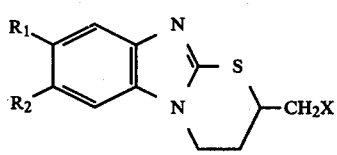

(I)

wherein R₁ and R₂ are each a hydrogen atom, an alkyl group having 1 to 6 carbon atoms, an alkoxy group having 1 to 6 carbon atoms or halogen atom, and X represents a hydroxy group, a tosyloxy group, an azide group, an alkylcarbonyloxy group having 1 to 6 carbon atoms, a trimethoxyphenylcarbonyloxy group, a thioether group, an alkyloxy group having 1 to 6 carbon atoms, an alkenyloxy group, a phenyloxy group, a benzyloxy group, a morpholino group,

wherein R₃ is a hydrogen atom or alkyl group having 1 to 6 carbon atoms, and R₄ is a hydrogen atom, an alkyl group having 1 to 6 carbon atoms, alkyl group having 1 to 2 carbon atoms and substituted by hydroxyl, alkyloxycarbonyl, cyclohexyl, furanyl or indolyl; phenyl which may be substituted by alkyl, alkoxy or halogen atom; benzyl, phenylamino,

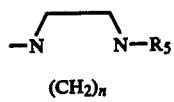

wherein $R_5$ represents a hydrogen atom, an alkyl group having 1 to 6 carbon atoms, hydroxyethyl, pyrrolidinocarbonylmethyl, pyrrolidinopropyl, trimethoxy phenylcarbonyloxypropyl or trimethoxyphenylcarbonyl, and n represents an integer of 2 or 3;

wherein m represents an integer of 4, 6 or 7; or piperidino which may be substituted by alkyl having 1 to 6 carbon atoms, hydroxy, alkyloxycarbonyl or benzyl.

* * * * *